United States Patent [19]

Stickler et al.

[11] 4,348,891

[45] Sep. 14, 1982

[54] TIRE HARDNESS TESTER

[75] Inventors: John M. Stickler, Stow; George L. Shook, Akron, both of Ohio

[73] Assignee: The B F Goodrich Company, New York, N.Y.

[21] Appl. No.: 231,207

[22] Filed: Feb. 4, 1981

[51] Int. Cl.³ ............................................. G01N 3/42
[52] U.S. Cl. ........................................ 73/81; 73/146
[58] Field of Search .................................... 73/81, 146

[56] References Cited

U.S. PATENT DOCUMENTS 2,812,583  11/1957  Herzegh ................................. 73/146
4,199,976   4/1980  Edward .................................. 73/81

FOREIGN PATENT DOCUMENTS 603531  10/1934  Fed. Rep. of Germany .......... 73/81

Primary Examiner—S. Clement Swisher
Attorney, Agent, or Firm—Joseph Januszkiewicz

[57] ABSTRACT

An apparatus for gauging the hardness of tire treads wherein a support member moveable supports a durometer which is connected to means for controlling the rate of descent of such a durometer to provide a constant predetermined force for measuring the hardness of a tire tread. A tire support supports a tire such that it is in alignment with the durometer.

12 Claims, 4 Drawing Figures

TIRE HARDNESS TESTER

BACKGROUND OF THE INVENTION

This invention relates to a tire testing device and more particularly to a device for accurately testing the hardness of the tread portion of a pneumatic tire with the use of a Tire Durometer.

In measuring the hardness of tires, it has been the practice for an operator to hand hold a durometer while measuring its hardness. The readings obtained can vary according to the operator's technique and the force exerted during the measuring process. It is an object of the present invention to assure a constant force applied by the measuring tool thus assuring an accurate reading, thus taking out variations and error due to the human operation.

SUMMARY OF THE INVENTION

The present invention is directed to an apparatus for gauging the hardness of tire treads. A support member provides an adjustable means for rotatably supporting a tire for presenting the upper portion of a tire tread to a durometer. The durometer is mounted on a moveable support connected to a dashpot to control the downward movement of the durometer at a controlled rate so that the durometer's penetrator impinges with a constant force. Gear means interconnects the dashpot via a cam to the moveable support to provide means for positioning the durometer for its controlled movement.

DETAILED DESCRIPTION

Figure 1:
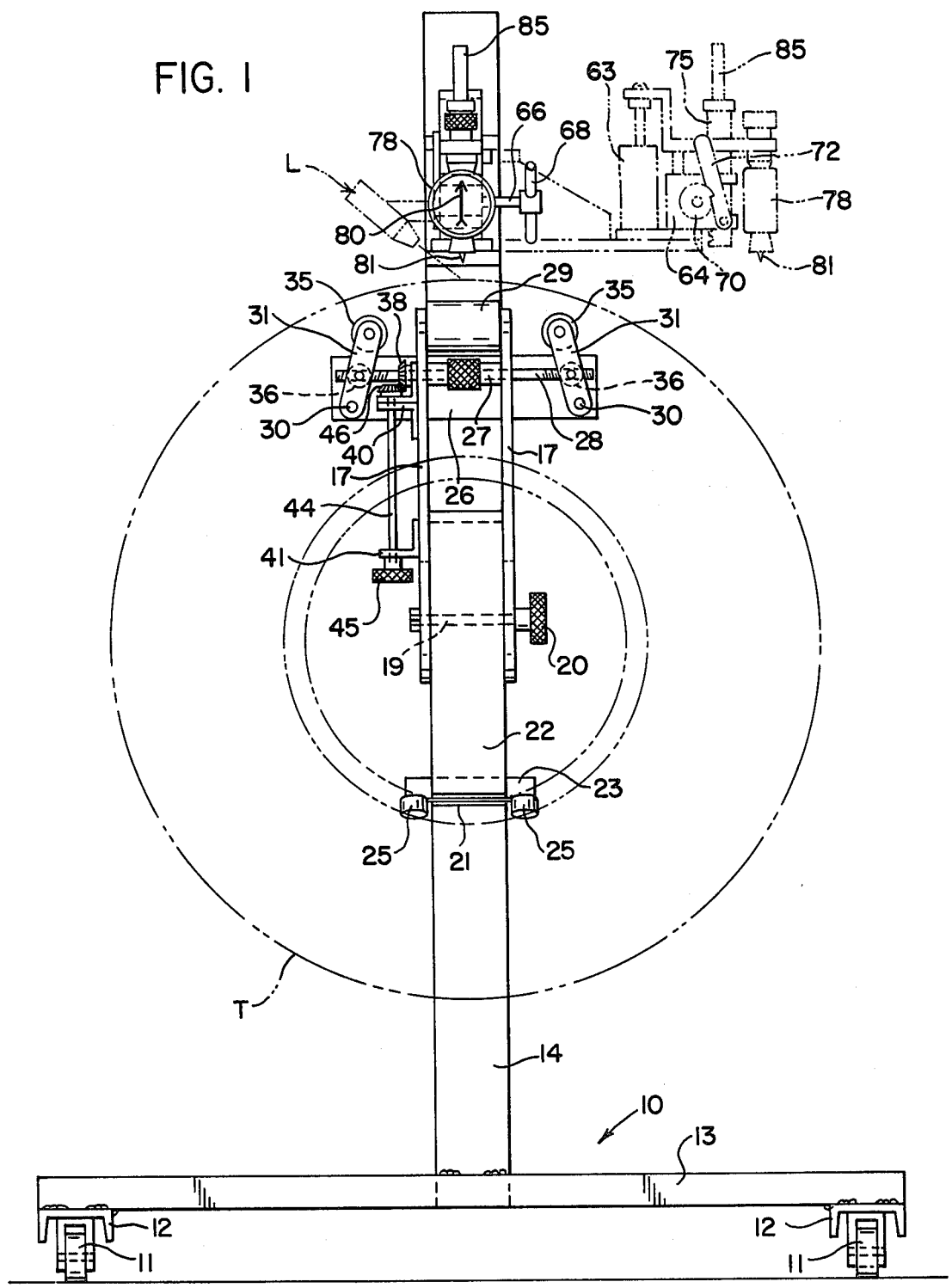
FIG. 1 is a front elevational view of a tire hardness tester with a tire shown in phantom lines.
Figure 2:
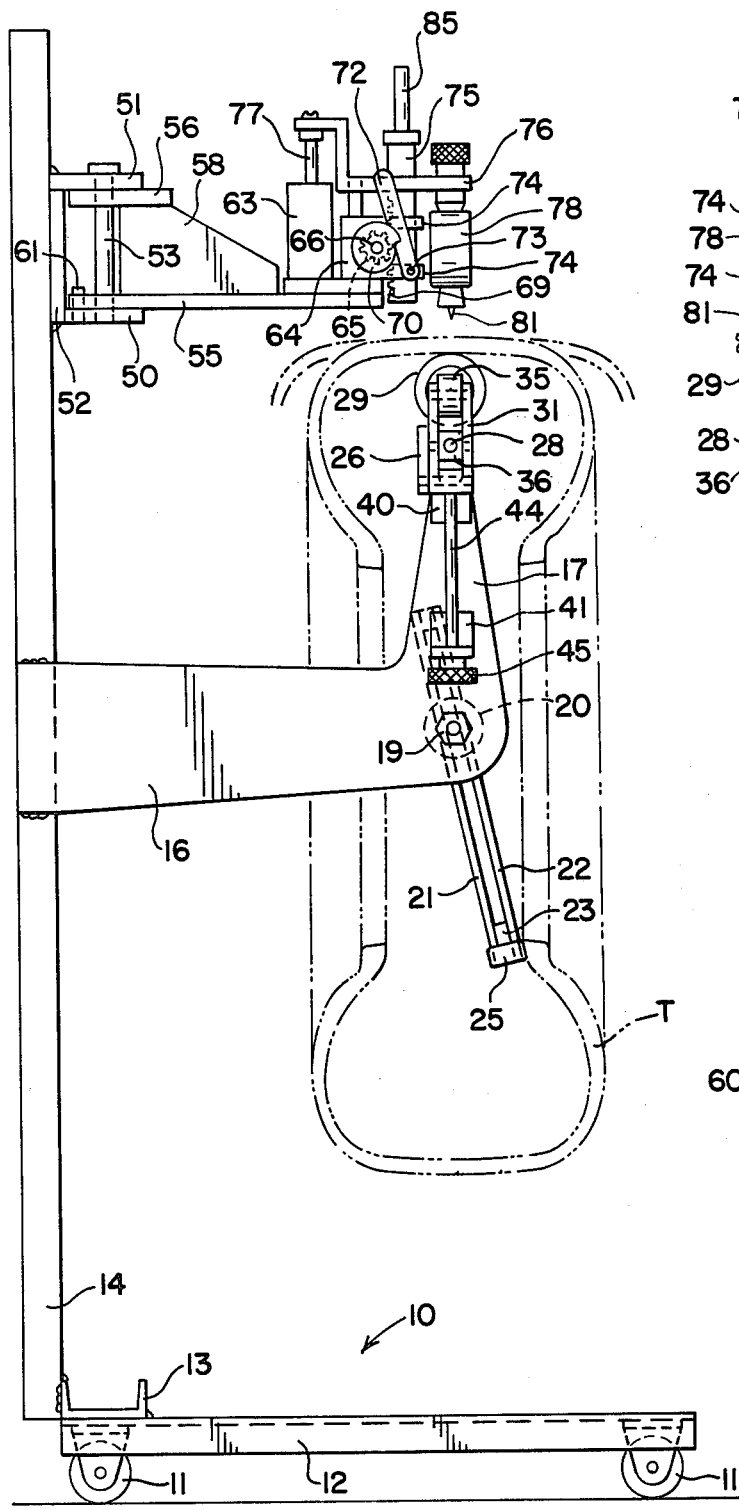
FIG. 2 is a side elevational view of the tire hardness tester with a tire shown in cross section.

Referring to the drawings, wherein like reference numerals designate like or corresponding parts throughout the several views, there is shown in FIGS. 1 and 2 a base 10 mounted on a plurality of rollers 11. Base 10 has a pair of parallel supports 12 interconnected at their rear by a channel frame member 13. Suitably secured to the frame member 13 is a vertically extending support member 14.

Secured to the intermediate portion of support member 14 are a pair of L-shaped members, each having a horizontally extending portion 16 and a vertically extending portions 17 (FIG. 2). The horizontal portions 16 are interconnected at their one ends by a threaded bolt 19 which has a knurled knob 20 thereon. A pair of flat parallel plates 21 and 22 slidably contact bolt 19. Plates 21 and 22 are joined at their upper ends by suitably means and joined at their lower ends by a plate member 23, which plate member 23 has a pair of spaced rollers 25 that are adapted to contact and support a tire T mounted thereon. Rotation of knob 20 locks the respective plate members 21 and 22 into their adjusted position by drawing the intermediate portion of the L-shaped member together. Such supports 16, 17, plates 21 and 22 and rollers 25.

The vertically extending end portions 17 are interconnected by a plate member 26. A bushing 27 is interposed between such upper end portions 17. A rod 28 is journaled for rotation in sleeve or bushing 27. The respective end portions of rod 28 which are threaded extend through the respective end portions 17. Pivotally mounted on the respective outboard end portions of plate member 26 as 30 are a pair of lever member 31. This respective adjacent lever members 31 have a roller 35 journaled on the uppermost end portions thereof and a threaded nut 36 secured to the intermediate portions thereof. The respective threaded end portions of rod 28 are of opposite hand such that rotation of rod 28 will move the respective nuts 36 and their corresponding lever members 31 and rollers 35 inwardly toward each other or away from each other in accordance with the direction of rotation of the rod 28. Bushing 27 is keyed to rod 28 to permit rotation of rod 28 but to prevent axial movement thereof. Suitably keyed to rod 28 and adjacent to an outer surface of one of the uppermost end portions 17 is a bevel gear 38. A pair of spaced brackets 40 and 41 are secured to the same end portion 17 of support member 14 as the bevel gear 38. A shaft 44 is journaled for rotation in brackets 40 and 41. The lower end portion of shaft 44 has a knob 45 secured thereto. The upper end portion of shaft 44 has a bevel gear 46 secured thereto for rotation therewith. Bevel gear 46 meshes with bevel gear 38 to effect rotation of rod 28. Rod 28 may be rotated by the knob 45 or the bushing 27. Mounted for rotation at the uppermost end portions 17 is a roller 29. Such supports 16, 17, plates 21 and 22, rollers 25, plate member 26, roller 29 and rollers 35 for a tire support means.

Secured to the upper end portion of support member 14 are a bracket means which included a pair of spaced horizontally disposed brackets 50 and 51 along with an interconnecting reinforcing member 52. A shaft or pin 53 extends through the respective brackets 50 and 51 and supports for pivotal movement thereon a pair of arm members 55 and 56. Arm members 55 and 56 are interconnected by a plate member 58. The one end portion of arm member 55 is recessed to provide a shoulder 60, which shoulder 60 is adapted to abuttingly engage a pin 61 mounted on bracket 50. Pin 61 operates as a stop to limit the pivotal movement of arm member 55 and its supporting structure to be described.

Mounted on the forward portion of arm member 55 is a dashpot 63 and a housing 64. Housing 64 journals for rotation a spur gear 65 and its shaft 66. The one end of shaft 66, exterior of the housing 64, has a handle 68 secured thereto. The other end of shaft 66, exterior of the housing 64, has a cam 70 secured thereto for rotation therewith. Cam 70 as seen in FIGS. 1 and 2 has a notch that is complimentary to a notch on stop lever 72. Lever 72 is pivotally mounted on housing 64 as at 73. Lever 72 rides on the surface of cam 70 until the respective notches coincide and engage thereby stopping the rotation of gear 65. An elongated plunger 75 guided by extensions 74—74 on housing 64 has a rack 69 which meshes with spur gear 65 and reciprocates with the rotation of gear 65. The arm members 55, 56, the housing 64 along with the gear 65, cam 70 and the lever 72 act as a durometer support means for control means to be described which control the movement of a durometer as it moves to and from a tire tread to be tested. A plunger 75 is secured to the intermediate portion of a carrier member or a plate member 76 for movement therewith. The one end of plate member 76 is secured to the piston rod 77 of accumlator or dashpot 63. The other end of plate member 76 has a durometer 78 mounted thereon. Durometers are gauges well known in the art to measure hardness, such as those manufactured by Shore and are commercially available on the market. Note U.S. Pat. Nos. 2,453,042 and 3,136,153. Durometer 78 has a gauge dial, a pointer 80 and a penetrator 81. To ascertain the hardness of a substances such as tread stock, the penetrator engages the substance to be measured and from the pressure applied by the durometer gauge, the hardness of the substance is measure by the resistance of the substance to the penetrator which is indicated by the pointer 80 on the face of the dial of the durometer as is well understood in the art. The plunger 75 has a reduced stem 85 on the upper end portion to receive weights if desired to provide a predetermined actuating force for the plunger 75 and the penetrator 81. With the plunger 75 and penetrator 81 interconnected directly to the stem 77 of the dashpot 63, the downward movement of the penetrator 81 is controlled at a precise controlled rate and force to provide consistent readings. The plunger 75 along with the plate member 76 and the dashpot 63 act as a control means for controlling the rate of descent of the durometer 78.

Figure 3:
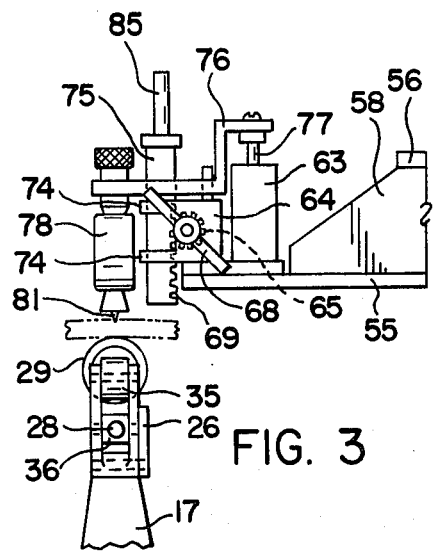
FIG. 3 is a side elevational view of a portion of the tire testing machine showing a portion of a tire carcass.
Figure 4:
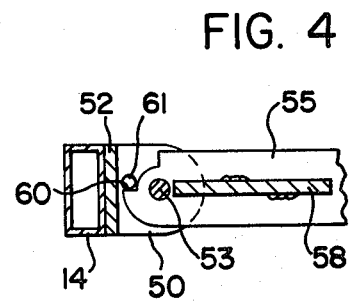
FIG. 4 is a fragmentary plan view of a pivotal support arm which carries the testing device.

In the operation of the above described apparatus, a tire T is placed over the rollers 35 and roller 29 such that the tread portion of such tire T that is to be tested is in directly alignment with the penetrator 81. Knob 20 is turned to release the locking tension of the movement of plates 21 and 22 such that plates 21 and 22 are positioned with rollers 25 engaging the bead area of the tire T as shown in FIG. 2. Knob 20 is rotated to tighten the tension of the horizontally extending portions 16 of the L-shaped member on plates 21 and 22 to lock such plates 21 and 22 in their desired position to maintain the tire T in its locked position. Handle 68 is then rotated in a counterclockwise direction as viewed in FIG. 3 which lowers the plunger 75 until it contacts the tread surface of the tire T. The handle 68 is then rotated in a clockwise direction as viewed in FIG. 3 until the notch 71 on cam 70 engages the notch in lever 72. This assures that upon release of lever 72 from notch 71 on cam 70, that before one full rotation of cam 70 is completed, the penetrator 81 will engage the tire tread of T and indicate on the dial of the durometer 78 the hardness of the tire tread. In the movement of the plunger 75, the penetrator 81 moves down slowly towards the tread since the plate 76 which is connected to the piston rod 77 acts on the oil in the dashpot 63. This action assures a uniform rate of descent and a consistent applied force on the sample being measured. A predetermined weight such as 9 pounds or whatever is desired may be placed on the rod 85. To take additional readings at various other locations on the tire tread, the operator rotates the handle 68 approximately one revolution until notch on the cam 70 engages the notch on the lever 72. The operation then rotates the tire to the next position and repeats the test by releasing the lever 72 as described above. As disclosed in FIG. 1 a light source L may be suitable secured to the housing 64 such that it projects a cross beam on the tire tread at the exact location where the durometer penetrator 81 will impinge or contact the tire tread to prevent erroneous readings caused by measuring the hardness too near a tread block edge. Befoe the tire T is removed from the test apparatus the durometer is swung out of the way by pivoting arm members 55 and 56 in a counterclockwise direction as viewed in FIG. 4, since stop 61 limits the clockwise rotation of arm member 55.

We claim:

1. An apparatus for gauging the hardness of tire treads comprising a support, said support having bracket means at the upper end thereof, a durometer support means mounted on said bracket means, a durometer mounted on said support means for vertical movement, said durometer having a penetrator for contact with a tire tread to provide a hardness reading on said durometer, control means mounted on said durometer support means and operatively connected to said durometer for controlling the movement of said durometer at a uniform rate of descent, a tire support means connected to said intermediate portion of said support for presenting an upper tread portion to said durometer, and said tire support means having a tread support member located on the inner peripheral surface of a tire in alignment with said penetrator of said durometer.

2. An apparatus for gauging the hardness of tire treads as set forth in claim 1 wherein said control means includes a dashpot connected to said durometer to control the descent of said durometer.

3. An apparatus for gauging the hardness of tire treads as set forth in claim 2 wherein said tire support means has a plurality of rollers for rotatable supporting said tire to provide means for presenting different portions of a tire tread to said durometer.

4. An apparatus for gauging the hardness of tire treads as set forth in claim 1 wherein said control means includes a plunger with a rack thereon, said rack meshing with a rotatable gear journaled on said support means, said control means includes a dashpot mounted interconnected to said plunger and said durometer to control the vertical movement thereof, and lock means connected to said plunger to control the limits of movement of said plunger and durometer.

5. An apparatus for gauging the hardness of tire treads as set forth in claim 4 wherein said lock means includes a lever pivotably mounted on said support means, and a cam connected to said gear for rotation therewith and for contact with said lever.

6. An apparatus for gauging the hardness of tire treads as set forth in claim 5 wherein said tire support means includes a plurality of rollers for supporting a tire, and one of said rollers being located in alignment with said penetrator and operative to frictionally contact the inner periphery of said tire.

7. An apparatus for gauging the hardness of tire treads as set forth in claim 6 wherein said durometer support means is pivotally connected to said bracket means and operative to swing said durometer support means away from said tire support means.

8. An apparatus for gauging the hardness of tire treads as set forth in claim 7 wherein said tire support means had an adjustable member for extension downwardly and laterally to contact the lower inner periphery of a tire to stabilize a tire on said tire support means.

9. An apparatus for gauging the hardness of tire treads as set forth in claim 8 wherein said plurality of rollers include at least a pair of laterally spaced adjustable rollers operative to support a tire for rotation thereon to present different portions of the tire tread surface to said penetrator.

10. An apparatus for gauging the hardness of tire treads, a support member, tire support means mounted on said support member for supporting the upper inner circumferential surface of a tire, said tire support means having lower longitudinally extending mounted thereof for adjustment downwardly and laterally for contact with the lower inner periphery of a tire to stabilize a tire thereon, a durometer support member mounted on said support member, said durometer support member having a housing thereon, a dashpot mounted on said durometer support member, a durometer with a penetrator mounted on said durometer support member for movement toward and away from the surface of a tire tread supported by said tire support means, and means interconnecting said dashpot and said durometer to control the uniform descent of said durometer and said penetrator.

11. An apparatus as set forth in claim 10 wherein said housing guides a reciprocal plunger connected to said means interconnecting said dashpot and said durometer for movement therewith, said housing has a gear journaled therein, said plunger having a gear rack meshing with said rotatable gear, and pawl means connected to said gear to limit the vertical and downward movement of said plunger and durometer.

12. An apparatus as set forth in claim 11 wherein a light beam source is mounted on said support member and projects and image on a tire tread at the exact location that said penetrator will contact said tread.

* * * * *